US006852743B1

(12) United States Patent
Ojima et al.

(10) Patent No.: US 6,852,743 B1
(45) Date of Patent: Feb. 8, 2005

(54) PREVENTIVES FOR THE RECURRENCE OF CEREBROVASCULAR FAILURE AND AGENTS FOR AMELIORATING TROUBLES FOLLOWING CEREBROVASCULAR FAILURE AND INHIBITING PROGRESS THEREOF

(75) Inventors: Mami Ojima, Amagasaki (JP);
Takahito Kitayoshi, Suita (JP);
Masaomi Miyamoto, Takarazuka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/031,398

(22) PCT Filed: Jul. 19, 2000

(86) PCT No.: PCT/JP00/04830

§ 371 (c)(1),
(2), (4) Date: Jan. 18, 2002

(87) PCT Pub. No.: WO01/05428

PCT Pub. Date: Jan. 25, 2001

(30) Foreign Application Priority Data

Jul. 21, 1999 (JP) ............................................ 11/205877

(51) Int. Cl.[7] ................. A61K 31/4184; A61K 31/4245
(52) U.S. Cl. ........................ 514/364; 514/381; 514/394; 514/395
(58) Field of Search ................................ 514/394, 395, 514/364, 381

(56) References Cited

U.S. PATENT DOCUMENTS

| 5,250,554 | A | * | 10/1993 | Naka et al. | 514/381 |
| 5,332,831 | A | * | 7/1994 | Dowle et al. | 548/315.4 |
| 5,519,138 | A | | 5/1996 | Ries et al. | 544/287 |
| 5,705,517 | A | * | 1/1998 | Naka et al. | 514/381 |
| 5,958,961 | A | * | 9/1999 | Inada et al. | 514/394 |
| 6,248,729 | B1 | * | 6/2001 | Coniglio et al. | 514/85 |
| 2004/0138278 | A1 | * | 7/2004 | Kueppers et al. | 514/381 |

FOREIGN PATENT DOCUMENTS

| DE | 41 42 366 A1 | 6/1993 |
| EP | 0 425 921 | 5/1991 |
| EP | 0 459 136 | 12/1991 |
| EP | 0 556 789 A2 | 8/1993 |
| EP | 0 881 212 | 12/1998 |
| WO | WO-94/11369 | * 5/1994 |
| WO | WO-97/37688 | * 10/1997 |
| WO | 00/02543 | 1/2000 |
| WO | 00/16773 | 3/2000 |

OTHER PUBLICATIONS

Sekine et al., Chemical Abstracts, 127:39817, 1997.*
Nagura et al., Chemical Abstracts, 125:25882, 1996.*
Stier et al., Chemical Abstracts, 119:62704, 1993.*
Juan M. Saavedra, "The Role of Angiotensin II in the Regulation of Cerebrovascular Function in the Rat", Pharm. Pharmacol. Lett., vol. 3, 1994, pp. 256–259, XP009000718.
J. Schrader et al., "Hypertension and Stroke—Rationale Behind the ACCESS Trial", Basic Research in Cardiology, vol. 93, No. Suppl. 2, 1998, pp. 69–78, XP001019616.
Masatoshi Fujishima, "Nou Kekkan Shougai no Hasshou, Saihatsu to sono Yobou", Ishiyaku Shuppan K.K., Igaku no Ayumi, vol. 188, No. 4, Jan. 23, 1999, pp. 217–222 (in Japanese).
Masaya Takahashi et al., "Therapeutic effects of imidapril on cerebral lesions observed by magnetic resonance imaging in malignant stroke–prone spontaneously hypertensive rats", Journal of Hypertension, 1994, vol. 12, No. 7, pp. 761–768.
Tsuneo Hasegawa, "Noukousoku Kanja no Rehabilitation; Kinou Hyouka to Rehabilitation no Susumekata", Kabkushiki Kaisha Nippon Rinshousha, CT, MRI Jidai no Nousocchu Gaku; Atarashii Shindan, Chiryou Taikei, vol. 1, Nov. 24, 1993, pp. 505–508 (in Japanese).

* cited by examiner

Primary Examiner—Fiona T. Powers
(74) Attorney, Agent, or Firm—Wenderoth, Lind & Ponack, L.L.P.

(57) ABSTRACT

There is provided an agent for preventing the recurrence of cerebrovascular disorder and an agent for ameliorating troubles following cerebrovascular disorder and inhibiting the progress thereof which contain a compound having an angiotensin II antagonistic activity, a prodrug thereof or a salts thereof.

5 Claims, No Drawings

PREVENTIVES FOR THE RECURRENCE OF CEREBROVASCULAR FAILURE AND AGENTS FOR AMELIORATING TROUBLES FOLLOWING CEREBROVASCULAR FAILURE AND INHIBITING PROGRESS THEREOF

This application is a 371 of PCT/JP00/04830 filed Jul. 19, 2000.

TECHNICAL FIELD

The present invention relates to an agent for preventing recurrence of cerebrovascular disorder comprising a compound having an angiotensin II antagonistic activity, a prodrug thereof or a salt thereof as an active ingredient, as well as an agent for ameliorating troubles following cerebrovascular disorder and inhibiting progress thereof comprising a compound having an angiotensin II antagonistic activity, a prodrug thereof or a salt thereof as an active ingredient.

BACKGROUND ART

According to the classification of cerebrovascular disorder, 3rd edition (MINDS-III, Stroke 21:637–676, 1990), National Institute of Neurological Disorders and Stroke (MINDS), cerebrovascular disorder is classified into asymptomatic cerebral infarction, transient ischemic attack (TIA), cerebral apoplexy, cerebrovascular dementia, and hypertensive encephalopathy. The type of cerebral apoplexy includes cerebral hemorrhage, subarachnoid hemorrhage, cranial hemorrhage accompanying a malformation in cerebral arteries and veins, and cerebral infarction, and there are many diseases causing each of them. In the past, hypertensive cerebral hemorrhage was a major disease, but by finding and managing hypertension at an early stage and westernization of nutrition intake, the rate of occurrence thereof and the death rate are gradually reduced, while the absolute number of old men with cerebral infarction and the ratio thereof are increasing due to spread of various kinds of image diagnosis techniques. Cerebral infarction is classified into atherothrombotic cerebral infarction, lacuna infarction, and cardiogenic cerebral infarction, among which lacuna infarction is decreasing with the progress of treatment of hypertension. On the other hand, the ratio of atherothrombotic cerebral infarction and cardiogenic cerebral infarction is increasing due to westernization of nutrition intake.

In Japan, these cerebrovascular disorders are at the second place of causes of death or at the top of causative diseases for bedridden old men at present, and thus countermeasures not only for prevention of occurrence of cerebrovascular disorder but also for prevention of recurrence thereof and progress of troubles following cerebrovascular disorder become important problems.

Medical treatment of cerebrovascular disorder is divided by a stage of diseases (acute stage, subacute stage, chronic stage, asymptomatic stage), a type of diseases (hemorrhagic, ischemic, etc.) and severity of diseases (presence or absence of hernia).

Treatment of cerebral apoplexy at an acute stage and a subacute stage includes systemic management including blood pressure, as well as inhibition of cerebral edema, measures against complications (hemorrhage in digestive tracts, infections in respiratory organs, convulsions, unrest, etc.), brain-protecting therapy (treatment by a brain-protecting drug, cryotherapy, etc.) and antithrombotic therapy depending on a particular type of diseases (treatment with thorombolytics, antiplatelets, anticoagulants, etc.), etc. For cerebral apoplexy at an acute stage, it is necessary to take a measure against cerebral edema in every type of diseases. Cerebral edema occurring at an acute stage of cerebrovascular disorder is a phenomenon in which the blood-brain barrier is disturbed by damage to brain, and fluid components in brain tissues are increased to increase the volume of brain, against which chemotherapy is generally conducted by intermittent administration of steroids or by intravenous injection of a hypertonic solution such as mannitol or glycerin. At an acute stage of cerebral apoplexy, in addition to a reactive increase in blood pressure, there are various changes in cerebral circulation kinetics, that is, a decrease in a cerebral blood flow rate not only in foci but also in a surrounding penambra region and in a part distant from foci in the brain, disorder in the ability for automatic regulation of cerebral blood flow, a reduction in $CO_2$ reactivity in cerebral vessels, etc. Accordingly, there is danger that a careless and significant reduction in blood pressure permits cerebral blood flow to be reduced depending on blood pressure and a penambra region can be exposed to irreversible danger. Then, use of an antihypertensive is restricted in principle, unless complications with severe hypertension and organ disorders attributable to hypertension such as heart failure are present. In the case of cerebral hemorrhage, however, there is danger of increasing hematocele, and thus about 20% reduction in blood pressure is often recommended, and in the case of subarachnoid hemorrhage, an increase in blood pressure causes re-bleeding and significantly influences the prognosis of life, and thus a durable depression in blood pressure is required.

Major medical treatment at a chronic stage involves a measure against troubles following cerebrovascular disorder and a measure for preventing recurrence thereof, depending on a particular type of diseases. The troubles following cerebrovascular disorder are classified roughly into nerve symptoms, mind symptoms, subjective symptoms (non-localizing subjective symptoms, localizing subjective symptoms, etc.), and obstacles in activities of daily living (ADL). In chemotherapy for these troubles following cerebrovascular disorder, nerve symptoms are limited to symptomatic therapy by an antispasmodic, etc. Chemotherapy is mainly directed to amelioration of nerve symptoms and subjective symptoms and uses agents for ameliorating cerebral circulation, agents for ameliorating cerebral metabolism (neurotransmission ameliorating agents, cerebral metabolism-activating agents, etc.) and psychotropics (anti-schizophrenia, anti-anxiety, antidepressant, etc.). Major treatment of obstacles in ADL involves rehabilitation, and chemotherapy is used as an aid to promote rehabilitation. Measures for preventing recurrence of cerebrovascular disorder include not only treatment (indirect measures) of diseases serving as factors causing hypertension, diabetes, hyperlipemia, etc., but also chemotherapy using antiplatelets, anti-coagulants, etc. depending on a particular type of diseases. However, there is no report suggesting that a compound having an AII antagonistic activity can be used in a direct measure for preventing recurrence of cerebrovascular disorder or for ameliorating troubles following cerebrovascular disorder and inhibiting progress thereof.

While treatment at an acute stage is the most important for treatment of cerebrovascular disorder from the viewpoint of medical economy, prevention of recurrence thereof and its progress are also major problems. However, only an antiplatelet is used for preventing recurrence of cerebrovascular disorder, and its usefulness is low.

The most dangerous factor for cerebrovascular disorder is hypertension, while the dangerous factors for cerebral infarction include an abnormality of sugar resistance and an abnormality in electrocardiogram, and the dangerous factors for cerebral hemorrhage include an abnormality in electrocardiogram, an abnormality in eye ground and drinking, and the like. As the dangerous factors for recurrence of cerebrovascular disorder, hypertension, cardiac disorders, TIA, diabetes, etc. are pointed out, and it can be considered that antihypertensive therapy is applied not only to prevention of occurrence of cerebrovascular disorder (primary prevention) but also to prevention of recurrence thereof (secondary prevention). However, usually hypertension accompanying cerebral apoplexy causes complications with diabetes, hyperlipemia and obesity, and accompanies high rates of vascular lesions in hearts, kidneys and peripheral arteries, and in such conditions, a presently existing antihypertensive therapy does not necessarily prevent the recurrence of cerebral apoplexy. This is because, in cerebral infarction after the onset, it is considered that cerebral arteriosclerotic lesions also proceed, and conventional antihypertensives cannot be expected to ameliorate such vascular lesions. Further, atherothrombotic cerebral infarction accompanying constriction and occlusion of a major stem artery occurs due to kinetics of the blood flow mechanism, so hypotension is considered to cause cerebral ischemia. In particular, the ability for automatic regulation of cerebral circulation has failed at an acute stage of cerebral apoplexy, and therefore rapid depression in blood pressure could conversely cause a reduction in cerebral blood flow to permit progress of cerebral ischemia. Further, at a chronic stage of 1 month or more after the onset of disease conditions, wherein antihypertensive therapy is usually initiated, the upper and lower limits of automatic regulation ability are deviated rightward (toward higher blood pressure level) in old men or patients with hypertension and cerebrovascular disorder, so even a slight depression in blood pressure causes a reduction in cerebral blood flow, to cause recurrence of cerebral ischemia. Further, patients with hypertension and cerebrovascular disorder often exhibit a non-dipper where blood pressure at night is increased even by administration of an antihypertensive, or an extra-dipper where blood pressure at night is too lowered, and hypertension is caused in early morning, and this change in blood pressure serves as a cause for inducing recurrence of cerebral apoplexy. Accordingly, there is demand for a drug having an anti-arteriosclerosis action, not lowering blood flow, improving the ability for automatic regulation of cerebral blood flow, and showing a stable and durable antihypertensive action.

At present, a long-lasting Ca antagonist or an angiotensin converting enzyme (ACE) inhibitor is used as an antihypertensive as a first choice in consideration of its action on cerebral circulation and cerebral vessels, and other drugs used include vasodilative β- or $α_1$-blockers. However, these drugs have problems with significant depression in blood pressure, duration of their action, and their side effects, and at present there is no ideal drug. Among them, due to a mechanism which is presumed to be attributable to a reduction in angiotensin II (AII) production in cerebral endarterium, the ACE inhibitor can particularly deviate the ability for automatic regulation of cerebral circulation leftward (toward lower blood pressure level), thus preventing or reducing cerebral ischemia developed by kinetics of the blood flow mechanism, and in this respect, the ACE inhibitor is a useful drug. However, the ACE inhibitor has the activity of not only inhibiting AII production but also decomposing inflammatory mediators such as bradykinin and substance P, and because of coughs and vascular edemas resulting therefrom, administration of the drug should inevitably be terminated in many cases. Further, an enlargement of edemas and cellular disorder may be induced due to enhancement of the inflammatory action, and particularly pathema at an acute stage (including ultra-acute stage to subacute stage) significantly influencing prognosis could be significantly worsened. Further, at present, there are little drugs (excellent in T/P ratio) showing stable depression in blood pressure through 24 hours, and in patients exhibiting a non-dipper having recurrence of cerebrovascular disorder at high rate or patients exhibiting hypertension in early morning, sufficiently stable depression in blood pressure cannot be achieved.

On the other hand, it is described that a compound having an antagonism to AII is known as an agent for treating diseases in circulatory organs, such as hypertension, cardiac diseases (cardiac hypertrophy, heart failure, myocardial infarction, etc.), cerebral apoplexy, nephritis, etc. (JP-A 4-364171, etc.), and it is demonstrated that AII having a strong vasoconstrictor action is prevented from acting on AII receptors by this compound to exhibit a durable action of depressing blood pressure.

Further, it is reported that Candesartan, i.e. an active metabolite of Candesartan cilexetil can deviate the lower limit of automatic regulation leftward (toward lower blood pressure level) (Vraamark T et al., J Hypertens 13:755–761, 1995), but there is no report suggesting that a compound having AII antagonistic activity is useful as an agent for preventing recurrence of cerebrovascular disorder or as an agent for ameliorating troubles following cerebrovascular disorder and inhibiting progress thereof.

DISCLOSURE OF THE INVENTION

The present invention provides pharmaceutical preparations useful for preventing recurrence of cerebrovascular disorder and for ameliorating troubles following cerebrovascular disorder and inhibiting progress thereof. Cerebrovascular disorder causes various troubles following the onset thereof, and therefore reduction of troubles following the cerebrovascular disorder and prevention the recurrence thereof are not only very important for a patient's comeback to normal life, but also can significantly contribute to a reduction in the number of bedridden old men or patients with vascular dementia, to significantly reduce medical expenses and the burden on the family.

Under the above-mentioned circumstances, the present inventors intensively studied pharmaceutical preparations useful for preventing recurrence of cerebrovascular disorder and for ameliorating troubles following cerebrovascular disorder and inhibiting progress thereof, and as a result, they found that a compound having an angiotensin II antagonistic activity, especially a compound represented by a specific structural formula and having angiotensin II (AII) antagonistic activity is very effective in preventing recurrence of cerebrovascular disorder and in ameliorating troubles following cerebrovascular disorder and inhibiting progress thereof, and as a result of further examination on the basis of these findings, the invention was completed.

That is, the present invention relates to:

(1) an agent for preventing recurrence of cerebrovascular disorder or an agent for ameliorating troubles following cerebrovascular disorder and inhibiting progress thereof which comprises a compound having an angiotensin II antagonistic activity (that is, a compound having an angiotensin II receptor antagonistic activity), a prodrug thereof or a salt thereof;

(2) the agent according to the above-mentioned (1), wherein the compound having an angiotensin II antagonistic activity is a non-peptide compound;
(3) the agent according to the above-mentioned (1), wherein the compound having an angiotensin II antagonistic activity is a compound having an oxygen atom in the molecule;
(4) the agent according to the above-mentioned (1), wherein the compound having an angiotensin II antagonistic activity is a compound having an ether bond or a carbonyl group:
(5) the agent according to the above-mentioned (1), wherein the compound having an angiotensin II antagonistic activity is a compound represented by the formula (I):

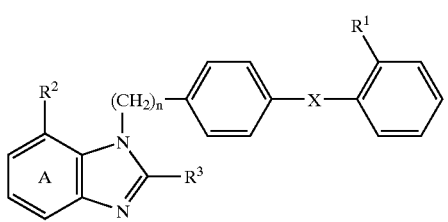

wherein $R^1$ represents a group capable of forming an anion or being converted into said group, X indicates that the phenylene group and the phenyl group are bound to each other directly or via a spacer of a chain made of 2 or less atoms, n is an integer of 1 or 2, ring A represents a benzene ring which may further have substituent(s), $R^2$ represents a group capable of forming an anion or being converted into said group, and $R^3$ represents a hydrocarbon residue which may be bound via a heteroatom and may have substituent(s);
(6) the agent according to the above-mentioned (1), wherein the compound having an angiotensin II antagonistic activity is Losartan, Eprosartan, Candesartan cilexetil, Candesartan, Valsartan, Telmisartan, Irbesartan, Olmesartan or Tasosartan;
(7) the agent according to the above-mentioned (1), wherein the compound having an angiotensin II antagonistic activity is 2-ethoxy-1-[[2'-(1H-tetrazole-5-yl)biphenyl-4-yl]methyl]benzimidazole-7-carboxylic acid;
(8) the agent according to the above-mentioned (1), wherein the compound having an angiotensin II antagonistic activity is 1-(cyclohexyloxycarbonyloxy)ethyl 2-ethoxy-1-[[2'-(1H-tetrazole-5-yl)biphenyl-4-yl]methyl]benzimidazole-7-carboxylate;
(9) the agent according to the above-mentioned (1), wherein the compound having an angiotensin II antagonistic activity is 2-ethoxy-1-[[2'-(2,5-dihydro-5-oxo-1,2,4-oxadiazole-3-yl)biphenyl-4-yl]methyl]benzimidazole-7-carboxylic acid;
(10) the agent according to the above-mentioned (1), wherein the troubles following cerebrovascular disorder are nerve symptoms;
(11) the agent according to the above-mentioned (1), wherein the troubles following cerebrovascular disorder are mental symptoms;
(12) the agent according to the above-mentioned (1), wherein the troubles following cerebrovascular disorder are subjective symptoms;
(13) the agent according to the above-mentioned (1), wherein the troubles following cerebrovascular disorder are obstacles in activities of daily living;
(14) use of a compound having an angiotensin II antagonistic activity, a prodrug thereof or a salt thereof for preventing recurrence of cerebrovascular disorder or in ameliorating troubles following cerebrovascular disorder or inhibiting progress thereof;
(15) use of a compound having an angiotensin II antagonistic activity, a prodrug thereof or a salt thereof for manufacturing a pharmaceutical preparation for preventing recurrence of cerebrovascular disorder or for ameliorating troubles following cerebrovascular disorder or inhibiting progress thereof;
(16) a method for preventing recurrence of cerebrovascular disorder in mammals which comprises administering an effective amount of a compound having an angiotensin II antagonistic activity, a prodrug thereof or a salt thereof to the mammals;
(17) a method for ameliorating troubles following cerebrovascular disorder or inhibiting progress thereof in mammals which comprises administering an effective amount of a compound having an angiotensin II antagonistic activity, a prodrug thereof or a salt thereof to the mammals;
(18) use of a compound having an angiotensin II antagonistic activity, a prodrug thereof or a salt thereof for manufacturing a pharmaceutical preparation for preventing recurrence of cerebrovascular disorder; and
(19) use of a compound having an angiotensin II antagonistic activity, a prodrug thereof or a salt thereof for manufacturing a pharmaceutical preparation for ameliorating troubles following cerebrovascular disorder or inhibiting progress thereof.

In the present invention, the compound having an angiotensin II antagonistic activity, a prodrug thereof or a salt thereof can be advantageously used for preventing recurrence of cerebrovascular disorder or ameliorating troubles following cerebrovascular disorder or inhibiting progress thereof, and for preventing occurrence of asymptomatic cerebral infarction or inhibiting transition thereof into symptomatic cerebral infarction, or for inhibiting transition of troubles following cerebrovascular disorder into cerebrovascular dementia.

The more specific action of the compound of the present invention having an angiotensin II antagonistic activity, a prodrug thereof or a salt thereof includes, for example, inhibition or amelioration of cerebral edema after cerebrovascular disorder; inhibition or amelioration of cellular disorder after cerebrovascular disorder; inhibition or amelioration of cerebral neuron disorder after cerebrovascular disorder; protection of brain after cerebrovascular disorder; inhibition or amelioration of endothelial cellular disorder after cerebrovascular disorder; inhibition or amelioration of infiltration of inflammatory cells or inflammation after cerebrovascular disorder; inhibition of promotion of free radical production from inflammatory cells, etc. after cerebrovascular disorder; inhibition of production and/or action of vascular agonists and thrombus inducers whose production increases after cerebrovascular disorder; amelioration of microcirculation after cerebrovascular disorder; inhibition of a promoting action on vascular penetration in cerebrovascular disorder; amelioration of disorder in the penambra region after cerebrovascular disorder; amelioration of the cerebral blood barrier after cerebrovascular disorder; inhibition of an increase in hematocrit (increase in blood viscosity) after cerebrovascular disorder; inhibition of formation of thrombi and emboli causing reoccurrence of cerebrovascular disorder; amelioration of vascular endothelial cell disorder causing reoccurrence of cerebrovascular disorder; amelioration of cardiac function disorder causing reoccurrence of cerebrovascular disorder, particularly cardiogenic cerebral infarction; amelioration of an abnormality in the transformability of erythrocytes after cerebrovascular disorder; inhibition of promotion of the agglutination ability of erythrocytes after cerebrovascular disorder; inhibition of promotion of the agglutination ability of platelets after cerebrovascular disorder; inhibition of promotion of the adherence ability of leukocytes after cerebrovascular disorder; inhibition or amelioration of the progress of arteriosclerosis foci in vascular lesions causing recurrence of cerebrovascular disorder, particularly cerebral infarction; etc.

In the present invention, the term "angiotensin II antagonistic activity" refers to the action of competitively or noncompetitively inhibiting binding of angiotensin II to angiotensin II receptors on cell membranes to attenuate strong vasoconstricting action and vascular smooth muscle proliferating action induced by angiotensin II to mitigate symptoms of hypertension.

The compound having an angiotensin II antagonistic activity used in the present invention may be a peptide or non-peptide compound, preferably a non-peptide antagonistic compound because of the advantage of long-lasting action. The compound having an angiotensin II antagonistic activity is preferably a compound having an oxygen atom in the molecule, particularly preferably a compound having an ether bond or a carbonyl group (said carbonyl group may form a hydroxyl group due to resonance), more preferably a compound having an ether bond or a ketone derivative, most preferably an ether derivative.

The non-peptide compounds having an angiotensin II antagonistic activity are not particularly limited, but, for example, imidazole derivatives are disclosed in JP-A 56-71073, JP-A 56-71074, JP-A 57-98270, JP-A 58-157768, U.S. Pat. Nos. 4,355,040 and 4,340,598; improved imidazole derivatives are disclosed in EP-253310, EP-291969, EP-324377, EP-403158, WO-9100277, JP-A 63-23868 and JP-A 1-117876; pyrrole, pyrazol and triazole derivatives are disclosed in U.S. Pat. No. 5,183,899, EP-323841, EP-409332 and JP-A 1-287071; benzimidazole derivatives are disclosed in U.S. Pat. No. 4,880,804, EP-0392317, EP-0399732, EP-0400835, EP-425921, EP-459136 and JP-A 3-63264; azaindene derivatives are disclosed in EP-399731 etc.; pyrimidone derivatives are disclosed in EP-407342 etc.; quinazoline derivatives are disclosed in EP-411766 etc.; xanthine derivatives are disclosed in EP-430300 etc.; condensed imidazole derivatives are disclosed in EP-434038 etc.; pyrimidine dione derivatives are disclosed in EP-442473 etc.; thienopyridone derivatives are disclosed in EP-443568 etc.; and heterocyclic compounds are disclosed in EP-445811, EP-483683, EP-518033, EP-520423, EP-588299 and EP-603712. Among these, representative compounds are also described in Journal of Medicinal Chemistry (Vol. 39, No. 3, pp. 625–656, 1996). As the non-peptide compounds having an angiotensin II antagonistic activity, it is possible to use, in addition to the compounds described above in the prior art literatures, any non-peptide compounds having an angiotensin II antagonistic activity, among which preferably used are Losartan (DuP753), Eprosartan (SK&F108566), Candesartan cilexetil (TCV-116), Valsartan (CGP-48933), Telmisartan (BIBR277), Irbesartan (SR47436) and Tasosartan (ANA-756), Olmesartan (CS-866), as well as active metabolites thereof (Candesartan, etc.), etc.

As the non-peptide compounds having an angiotensin II antagonistic activity, it is also preferable to employ, for example, a benzimidazole derivative represented by the formula (I):

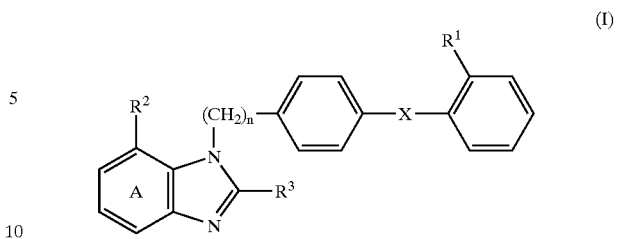

(I)

wherein $R^1$ represents a group capable of forming an anion or being converted into said group, X indicates that the phenylene group and the phenyl group are bound to each other directly or via a spacer of a chain made of 2 or less atoms, n is an integer of 1 or 2, ring A represents a benzene ring which may further have substituent(s), $R^2$ represents a group capable of forming an anion or being converted into said group, and $R^3$ represents a hydrocarbon residue which may be bound via a heteroatom and may have substituent(s) (preferably a hydrocarbon residue which is bound via an oxygen atom and may have substituent(s)) or a salt thereof.

As $R^1$ in the above-mentioned formula (I), the group capable of forming an anion (that is, a group having a hydrogen atom releasable as a proton) includes, for example, (1) a carboxyl group, (2) a tetrazolyl group, (3) a trifluoromethanesulfonic acid amide group ($—NHSO_2CF_3$), (4) a phosphate group, (5) a sulfonate group, (6) a 5- to 7-membered (preferably 5- to 6-membered) monocyclic, optionally substituted heterocyclic residue containing at least one atom selected from N, S and O.

Examples of the "5- to 7-membered (preferably 5- to 6-membered) monocyclic, optionally substituted heterocyclic residue containing at least one atom selected from N, S and O" include:

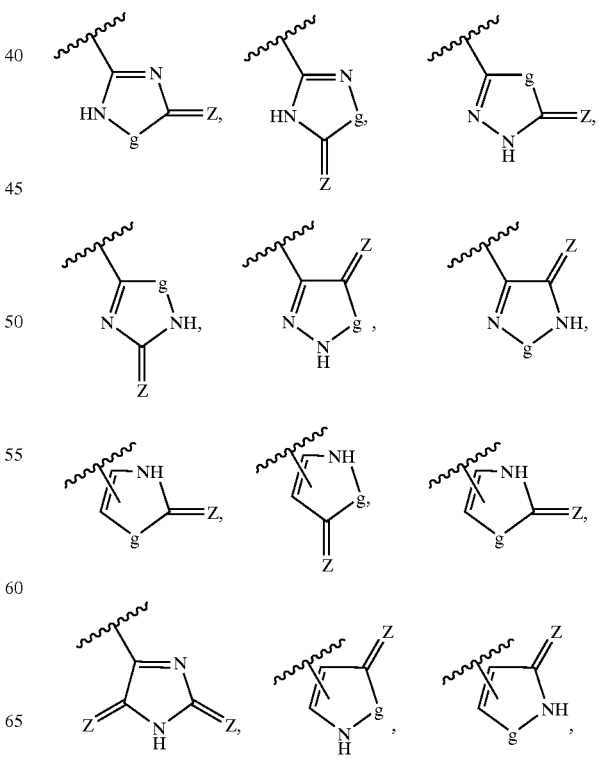

-continued

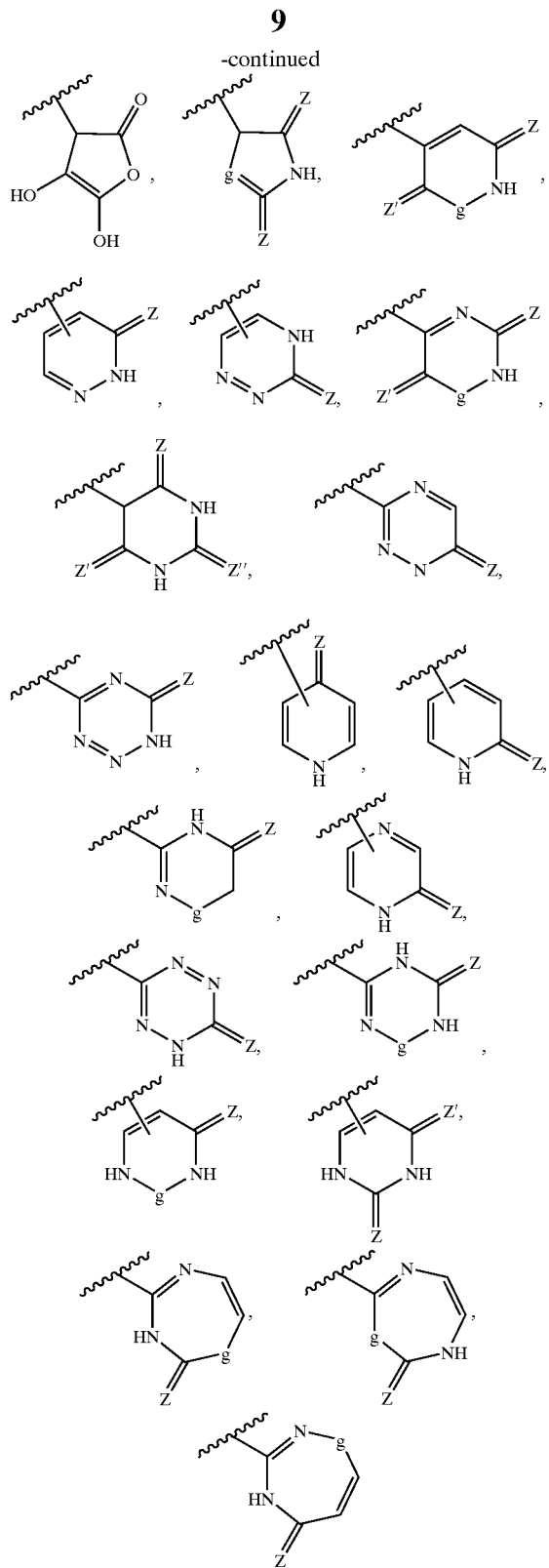

and the like.

In the formulas above, when g represents —NH— etc., the bond between the heterocyclic residue represented by $R^1$ and the phenyl group to which the heterocyclic residue is bound may be not only the carbon-carbon bond, but also one of plural nitrogen atoms present therein. For example, if $R^1$ is represented by:

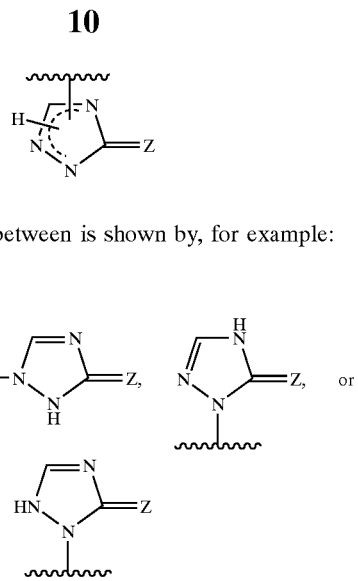

then, the bond therebetween is shown by, for example:

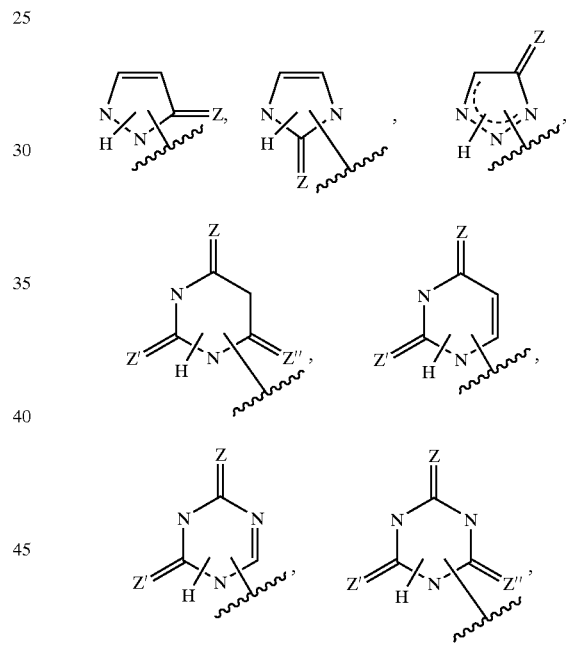

Other examples of such bonds via a nitrogen atom include:

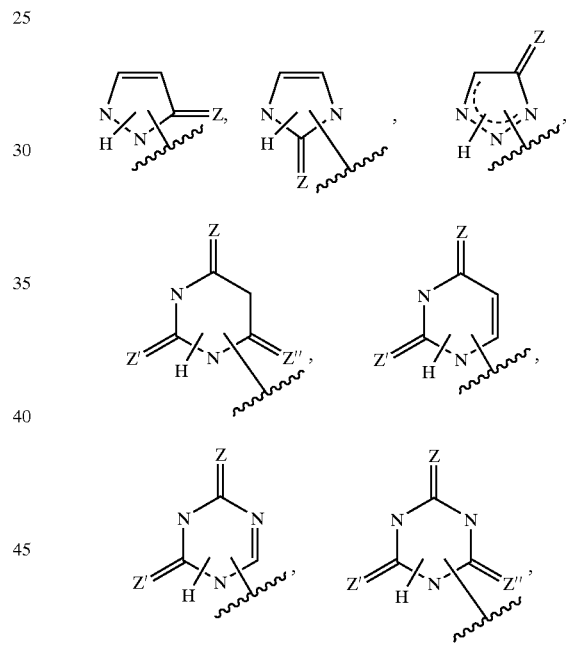

and the like.

In the formulas above, g represents —CH$_2$—, —NH—, —O— or —S(O)$_m$—; >=Z, >=Z' and >=Z" represent a carbonyl group, a thiocarbonyl group and an optionally oxidized sulfur atom (e.g., S, S(O), S(O)$_2$ etc.) (preferably a carbonyl or thiocarbonyl group, more preferably a carbonyl group) respectively; and m is an integer of 0, 1 or 2.

Preferably, the heterocyclic residue represented by $R^1$ is, for example, a group having both an —NH— or —OH— group as a proton donor such as in an oxadiazolone ring, an oxadiazolothion ring or a thiadiazolone ring and a carbonyl group, a thiocarbonyl group or a sulfinyl group as a proton acceptor. Further, the heterocyclic residue represented by $R^1$ may form a condensed ring by binding a cyclic substituent thereto, but the heterocyclic residue represented by $R^1$ is preferably a 5- to 6-membered ring, more preferably a 5-membered ring.

The heterocyclic ring represented by $R^1$ is preferably a group represented by the formula:

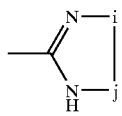

wherein i represents —O— or —S—, j represents >=O, >=S or >=S(O)$_m$ wherein m has the same meanings as defined above, and said heterocyclic ring is particularly preferably 2,5-dihydro-5-oxo-1,2,4-oxadiazole-3-yl, 2,5-dihydro-5-thioxo-1,2,4-oxadiazole-3-yl, 2,5-dihydro-5-oxo-1,2,4-thiadiazole-3-yl, especially 2,5-dihydro-5-oxo-1,2,4-oxadiazole-3-yl.

As the above heterocyclic residue ($R^1$), tautomers are present as shown below. For example, in the case of:

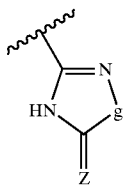

wherein Z=O and g=O, there occur three a', b' and c' tautomers as shown below:

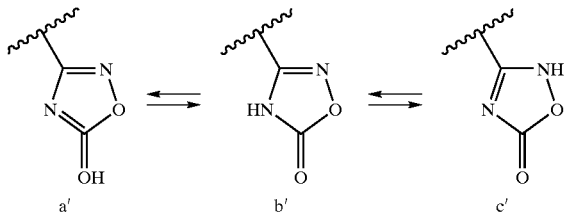

and the heterocyclic residue represented by:

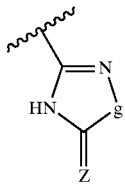

includes all the a', b' and c' mentioned above.

As $R^1$, the group capable of forming an anion may have been protected at replaceable positions by an optionally substituted lower ($C_{1-4}$) alkyl group or an acyl group (e.g., lower ($C_{2-5}$) alkanoyl, benzoyl etc.).

The optionally substituted lower ($C_{1-4}$) alkyl group includes, for example, (1) a lower ($C_{1-4}$) alkyl group which may be substituted with 1 to 3 phenyl groups which may have a halogen atom, nitro, lower ($C_{1-4}$) alkyl, lower ($C_{1-4}$) alkoxy etc. (e.g., methyl, triphenylmethyl, p-methoxybenzyl, p-nitrobenzyl etc.), (2) a lower ($C_{1-4}$) alkoxy-lower ($C_{1-4}$) alkyl group (e.g., methoxymethyl, ethoxymethyl etc.), and (3) the formula —CH($R^4$)—OCOR$^5$ wherein $R^4$ represents (a) hydrogen, (b) a $C_{1-6}$ straight or branched lower alkyl group (e.g., methyl, ethyl, n-propyl, isopropyl, n-butyl, isobutyl, t-butyl, n-pentyl, isopentyl, neopentyl etc.), (c) a $C_{2-6}$ straight or branched lower alkenyl group or (d) a $C_{3-8}$ cycloalkyl group (e.g., cyclopentyl, cyclohexyl, cycloheptyl etc.), and $R^5$ represents (a) a $C_{1-6}$ straight or branched lower alkyl group (e.g., methyl, ethyl, n-propyl, isopropyl, n-butyl, isobutyl, sec-butyl, t-butyl, n-pentyl, isopentyl, neopentyl etc.), (b) a $C_{2-6}$ straight or branched lower alkenyl group, (c) a $C_{1-3}$ lower alkyl group which may be substituted with a $C_{3-8}$ cycloalkyl group (e.g., cyclopentyl, cyclohexyl, cycloheptyl etc.) or with an aryl group which may be substituted (e.g., a phenyl or naphthyl group which may have a halogen atom, nitro, lower ($C_{1-4}$) alkyl, lower ($C_{1-4}$) alkoxy etc.) (e.g., benzyl, p-chlorobenzyl, phenethyl, cyclopentylmethyl, cyclohexylmethyl etc.), (d) a $C_{2-3}$ lower alkenyl group substituted with $C_{3-8}$ cycloalkyl or with an aryl group which may be substituted (e.g., a phenyl or naphthyl group which may have a halogen atom, nitro, lower ($C_{1-4}$) alkyl, lower ($C_{1-4}$) alkoxy etc.) (e.g., a group such as cinnamyl having an alkenyl moiety such as vinyl, propenyl, allyl, isopropenyl etc.), (e) an aryl group which may be substituted (e.g., a phenyl or naphthyl group which may have a halogen atom, nitro, lower ($C_{1-4}$) alkyl, lower ($C_{1-4}$) alkoxy etc., such as phenyl, p-tolyl, naphthyl etc.), (f) a $C_{1-6}$ straight or branched lower alkoxy group (e.g., methoxy, ethoxy, n-propoxy, isopropoxy, n-butoxy, isobutoxy, sec-butoxy, t-butoxy, n-pentyloxy, isopentyloxy, neopentyloxy etc.), (g) a $C_{2-8}$ straight or branched lower alkenyloxy group (e.g., allyloxy, isobutenyloxy etc.), (h) a $C_{3-8}$ cycloalkyloxy group (e.g., cyclopentyloxy, cyclohexyloxy, cycloheptyloxy etc.), (i) a $C_{1-3}$ lower alkoxy group substituted with a $C_{3-8}$ cycloalkyl (e.g., cyclopentyl, cyclohexyl, cycloheptyl etc.) or with an aryl group which may be substituted (e.g., a phenyl or naphthyl group which may have a halogen atom, nitro, lower ($C_{1-4}$) alkyl, lower ($C_{1-4}$) alkoxy etc.) (e.g., a group such as benzyloxy, phenethyloxy, cyclopentylmethoxy, cyclohexyl methoxy etc. having an alkoxy moiety such as methoxy, ethoxy, n-propoxy, isopropoxy etc.), (j) a $C_{2-3}$ lower alkenyloxy group substituted with a $C_{3-8}$ cycloalkyl (e.g., cyclopentyl, cyclohexyl, cycloheptyl etc.) or with an aryl group which may be substituted (e.g., a phenyl or naphthyl group which may have a halogen atom, nitro, lower ($C_{1-4}$) alkyl, lower ($C_{1-4}$) alkoxy etc.) (e.g., a group such as cinnamyloxy etc. having an alkenyloxy moiety such as vinyloxy, propenyloxy, allyloxy, isopropenyloxy etc.), or (k) an aryloxy group which may be substituted (e.g., a phenoxy or naphthoxy group which may have a halogen atom, nitro, lower ($C_{1-4}$) alkyl, lower ($C_{1-4}$) alkoxy etc. such as phenoxy, p-nitrophenoxy, naphthoxy etc.).

As $R^1$, the group capable of forming an anion may have, in addition to the protective group such as an optionally substituted lower ($C_{1-4}$) alkyl group or an acyl group (e.g., lower ($C_{2-5}$) alkanoyl, benzoyl etc.), substituent(s) such as a lower ($C_{1-4}$) alkyl group which may be substituted (the same as the "lower ($C_{1-4}$) alkyl group which may be substituted" exemplified with respect to the above protective group for the group capable of forming an anion represented by $R^1$), a halogen atom, nitro, cyano, and amino which may be substituted with one or two lower ($C_{1-4}$) alkyl groups, at replaceable positions.

As $R^1$ in the above-mentioned formula, the group capable of being converted into the group capable of forming an anion (the group having a hydrogen atom releasable as a proton) may also be a group which can be converted into the group capable of forming an anion under biological, that is, physiological conditions (e.g., reactions in the living body, such as oxidation, reduction or hydrolysis by enzymes in the living body) (so-called a prodrug), or it also may be a group such as (1) a carboxyl group, (2) a tetrazolyl group, (3) a trifluoromethanesulfonic acid amide group (—NHSO$_2$CF$_3$), (4) a phosphate group, (5) a sulfonate group, (6) a 5- to 7-membered (preferably 5- to 6-membered) monocyclic, optionally substituted heterocyclic residue containing at least one atom selected from N, S and O, which are protected with cyano, a N-hydroxycarbamimidoyl group (—C(=N—OH)—NH$_2$), an optionally substituted lower (C$_{1-4}$) alkyl group, and an acyl group respectively, and which can be converted by chemical reaction into the group capable of forming an anion represented by R$^1$ (so-called a synthetic intermediate).

Preferably, R$^1$ is carboxyl which may be protected with an optionally substituted lower (C$_{1-4}$) alkyl (e.g., methyl, triphenylmethyl, methoxymethyl, ethoxymethyl, p-methoxybenzyl, p-nitrobenzyl etc.) or with an acyl group (e.g., lower (C$_{2-5}$) alkanoyl, benzoyl etc.); tetrazolyl or 2,5-dihydro-5-oxo-1,2,4-oxadiazole-3-yl (preferably, tetrazolyl); or cyano, N-hydroxycarbamimidoyl (preferably, cyano), among which cyano is particularly preferably used.

In the above-mentioned formula, X indicates that the phenylene group and the phenyl group are bound to each other directly or via a spacer of a chain made of 2 or less atoms (preferably a direct bond). The spacer of a chain made of 2 or less atoms may be any divalent chain and may have a side chain insofar as the number of atoms constituting the straight chain is 1 or 2. Specifically, it is lower (C$_{1-4}$) alkylene having a straight chain consisting of 1 or 2 carbon atoms, —CO—, —O—, —S—, —NH—, —CO—NH—, —O—CH$_2$—, —S—CH$_2$—, —CH=CH—, etc.

In the above-mentioned formula, n is an integer of 1 or 2, preferably 1.

In the formula, ring A represents a benzene ring which may further have substituent(s) other than the substituent group R$^2$, and said substituent includes, for example, (1) halogen (e.g., F, Cl, Br etc.), (2) cyano, (3) nitro, (4) lower (C$_{1-4}$) alkyl which may be substituted, (5) lower (C$_{1-4}$) alkoxy, (6) an amino group which may be substituted (e.g., amino, N-lower (C$_{1-4}$) alkylamino (e.g., methylamino), N,N-di-lower (C$_{1-4}$) alkylamino (e.g., dimethylamino etc.), N-arylamino (e.g., phenylamino etc.), alicyclic amino (e.g., morpholino, piperidino, piperazino, N-phenylpiperazino etc.) etc.), (7) a group represented by the formula —CO—D' wherein D' represents a hydroxyl group or a lower (C$_{1-4}$) alkoxy which may be substituted at its alkyl moiety by a hydroxyl group, a lower (C$_{1-4}$) alkoxy, lower (C$_{2-6}$) alkanoyloxy (e.g., acetoxy, pivaloyloxy etc.), lower (C$_{1-6}$) alkoxycarbonyloxy (e.g., methoxycarbonyloxy, ethoxycarbonyloxy etc.) or lower (C$_{3-6}$) cycloalkoxycarbonyloxy (e.g., cyclohexyloxycarbonyloxy etc.), or (8) tetrazolyl, a trifluromethanesulfonic acid amido group, a phosphate group or a sulfonate group which may be protected with acyl (e.g., lower (C$_{2-5}$) alkanoyl, benzoyl etc.) or with lower (C$_{1-4}$) alkyl which may be substituted (the same as the "lower (C$_{1-4}$) alkyl group which may be substituted" exemplified with respect to the protective group for the group capable of forming an anion represented by R$^1$), and the like.

The benzene ring may have been substituted at replaceable positions thereof with one or two of these substituents groups. The substituent which is possessed by A in addition to the substituent represented by R$^2$ is preferably a lower (C$_{1-4}$) alkyl which may be substituted (e.g., lower (C$_{1-4}$) alkyl which may be substituted with a hydroxyl group, carboxyl group, halogen etc.), halogen etc., and more preferably, ring A does not have a substituent other than the substituent represented by R$^2$.

In the above-mentioned formula, the group capable of forming an anion represented by R$^2$ (that is, a group having a hydrogen atom releasable as a proton) includes, for example, (1) a carboxyl group which may be esterified or amidated, (2) a tetrazolyl group, (3) a trifluoromethanesulfonic acid amide group (—NHSO$_2$CF$_3$), (4) a phosphate group and (5) a sulfonate group, etc. and these may have been protected with a lower alkyl group which may be substituted (the same as the "lower (C$_{1-4}$) alkyl group which may be substituted" exemplified with respect to the protective group for the group capable of forming an anion represented by R$^1$) or an acyl group (e.g., lower (C$_{2-5}$) alkanoyl, benzoyl etc.), and may be any group capable of forming an anion or being converted into said group chemically or biologically i.e. under physiological conditions (e.g., reactions in the living body, such as oxidation, reduction or hydrolysis in enzymes in the living body).

As R$^2$, the carboxyl which may be esterified or amidated includes, for example, groups represented by the formula —CO—D wherein D represents (1) a hydroxyl group, (2) amino which may be substituted (e.g., amino, N-lower (C$_{1-4}$) alkylamino, N,N-di-lower (C$_{1-4}$) alkylamino etc.) or (3) alkoxy which may be substituted {e.g., (i) a lower (C$_{1-6}$) alkoxy group which may be substituted at its alkyl moiety by a hydroxyl group, amino which may be substituted (e.g., amino, N-lower (C$_{1-4}$) alkylamino, N,N-di-lower (C$_{1-4}$) alkylamino, piperidino, morpholino etc.), halogen, lower (C$_{1-6}$) alkoxy, lower (C$_{1-6}$) alkylthio, lower (C$_{3-8}$) cycloalkoxy, or dioxolenyl which may be substituted (e.g., 5-methyl-2-oxo-1,3-dioxolene-4-yl etc.), or (ii) groups represented by the formula —O—CH(R$^6$)—OCOR$^7$ wherein R$^6$ represents (a) hydrogen, (b) a C$_{1-6}$ straight or branched lower alkyl group (e.g., methyl, ethyl, n-propyl, isopropyl, n-butyl, isobutyl, t-butyl, n-pentyl, isopentyl, neopentyl etc.), (c) a C$_{2-6}$ straight or branched lower alkenyl group or (d) a C$_{3-8}$ cycloalkyl group (e.g., cyclopentyl, cyclohexyl, cycloheptyl etc.), and R$^7$ represents (a) a C$_{1-6}$ straight or branched lower alkyl group (e.g., methyl, ethyl, n-propyl, isopropyl, n-butyl, isobutyl, sec-butyl, t-butyl, n-pentyl, isopentyl, neopentyl etc.), (b) a C$_{2-6}$ straight or branched lower alkenyl group, (c) a C$_{1-3}$ lower alkyl substituted with a C$_{3-8}$ cycloalkyl group (e.g., cyclopentyl, cyclohexyl, cycloheptyl etc.) or with an aryl group which may be substituted (e.g., a phenyl or naphthyl group which may have a halogen atom, nitro, lower (C$_{1-4}$) alkyl, lower (C$_{1-4}$) alkoxy etc.) group (e.g., benzyl, p-chlorobenzyl, phonetic, cyclopentylmethyl, cyclohexylmethyl etc.), (d) a C$_{2-3}$ lower alkenyl group substituted with C$_{3-8}$ cycloalkyl or with an aryl group which may be substituted (e.g., a phenyl or naphthyl group which may have a halogen atom, nitro, lower (C$_{1-4}$) alkyl, lower (C$_{1-4}$) alkoxy etc.) (e.g., a group such as cinnamyl having an alkenyl moiety such as vinyl, propenyl, allyl, isopropenyl etc.), (e) an aryl group which may be substituted (e.g., a phenyl or naphthyl group such as phenyl, p-tolyl, naphthyl etc., which may have a halogen atom, nitro, lower (C$_{1-4}$) alkyl, lower (C$_{1-4}$) alkoxy etc.), (f) a C$_{1-6}$ straight or branched lower alkoxy group (e.g., methoxy, ethoxy, n-propoxy, isopropoxy, n-butoxy, isobutoxy, sec-butoxy, t-butoxy, n-pentyloxy, isopentyloxy, neopentyloxy etc.), (g) a C$_{2-8}$ straight or branched lower alkenyloxy group (e.g., allyloxy, isobutenyloxy etc.), (h) a C$_{3-8}$ cycloalkyloxy group (e.g., cyclopentyloxy, cyclohexyloxy, cycloheptyloxy etc.), (i) a C$_{1-3}$ lower alkoxy group substituted with a C$_{3-8}$ cycloalkyl (e.g., cyclopentyl, cyclohexyl, cycloheptyl etc.) or with an aryl group which may be substituted (e.g., a phenyl or naphthyl group which may have a halogen atom, nitro, lower (C$_{1-4}$) alkyl, lower (C$_{1-4}$) alkoxy etc.) (e.g., a group such as benzyloxy, phenethyloxy, cyclopentylmethoxy, cyclohexylmethoxy etc. having an alkoxy moiety such as methoxy, ethoxy, n-propoxy, isopropoxy etc.), (j) a $C_{2-3}$ lower alkenyloxy group substituted with a $C_{3-8}$ cycloalkyl (e.g., cyclopentyl, cyclohexyl, cycloheptyl etc.) or with an aryl group which may be substituted (e.g., a phenyl or naphthyl group which may have a halogen atom, nitro, lower ($C_{1-4}$) alkyl, lower ($C_{1-4}$) alkoxy etc.) (e.g., a group such as cinnamyloxy etc. having an alkenyloxy moiety such as vinyloxy, propenyloxy, allyloxy, isopropenyloxy etc.), or (k) an aryloxy group which may be substituted (e.g., a phenoxy or naphthoxy group which may have a halogen atom, nitro, lower ($C_{1-4}$) alkyl, lower ($C_{1-4}$) alkoxy etc. such as phenoxy, p-nitrophenoxy, naphthoxy etc.).

$R^2$ is preferably carboxyl which may be esterified, and examples thereof include —COOH and a salt thereof, —COOMe, —COOEt, —COOtBu, —COOPr, pivaloyloxymethoxycarbonyl, 1-(cyclohexyloxycarbonyloxy) ethoxycarbonyl, 5-methyl-2-oxo-1,3-dioxolene-4-ylmethoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy) ethoxycarbonyl, 1-(isobutyryloxy)ethoxycarbonyl, cyclohexylcarbonyloxymethoxycarbonyl, benzoyloxymethoxycarbonyl, cinnamyloxycarbonyl, cyclopentylcarbonyloxymethoxycarbonyl etc., and $R^2$ may be any group capable of forming an anion (e.g., COO—, derivatives thereof, etc.) or being converted into said group chemically or biologically i.e. under physiological conditions (e.g., reactions in the living body, such as oxidation, reduction or hydrolysis by enzymes in the living body) or may be a carboxyl group or a prodrug thereof.

$R^2$ is preferably a group represented by the formula —CO—D wherein D represents (1) a hydroxyl group or (2) a lower ($C_{1-4}$) alkoxy which may be substituted at its alkyl moiety by a hydroxyl group, amino, halogen, lower ($C_{2-6}$) alkanoyloxy (e.g., acetoxy, pivaloyloxy etc.), lower ($C_{3-8}$) cycloalkanoyloxy, lower ($C_{1-6}$) alkoxycarbonyloxy (e.g., methoxycarbonyloxy, ethoxycarbonyloxy etc.), lower ($C_{3-8}$) cycloalkoxycarbonyloxy (e.g., cyclohexyloxycarbonyloxy etc.), lower ($C_{1-4}$) alkoxy or lower ($C_{3-8}$) cycloalkoxy, and carboxyl esterified with lower ($C_{1-4}$) alkyl (preferably methyl or ethyl) is preferable.

In the above-mentioned formula, the "hydrocarbon residue" in the "hydrocarbon residue which may be bound via a heteroatom and may have a substituent group" represented by $R^3$ includes e.g. (1) an alkyl group, (2) an alkenyl group, (3) an alkynyl group, (4) a cycloalkyl group, (5) an aryl group, (6) an aralkyl group and the like, among which an alkyl group, an alkenyl group and a cycloalkyl group are preferable.

The alkyl group in the above-mentioned (1) is a lower alkyl group containing about 1 to 8 carbon atoms which may be straight or branched, and examples thereof include methyl, ethyl, propyl, isopropyl, butyl, isobutyl, sec-butyl, t-butyl, pentyl, i-pentyl, hexyl, heptyl and octyl.

The alkenyl group in the above-mentioned (2) is a straight or branched lower alkenyl group containing about 2 to 8 carbon atoms, and examples thereof include vinyl, propenyl, 2-butenyl, 3-butenyl, isobutenyl, 2-octenyl etc.

The alkynyl group in the above-mentioned (3) is a lower alkynyl group containing about 2 to 8 carbon atoms which may be straight or branched, and examples thereof include ethynyl, 2-propynyl, 2-butynyl, 2-pentynyl, 2-octynyl etc.

The cycloalkyl group in the above-mentioned (4) includes a lower cycloalkyl containing about 3 to 6 carbon atoms, and examples thereof include cyclopropyl, cyclobutyl, cyclopentyl, cyclohexyl etc.

The above-mentioned alkyl group, alkenyl group, alkynyl group or cycloalkyl group may have been substituted with a hydroxyl group, an amino group which may be substituted (e.g., amino, N-lower ($C_{1-4}$) alkylamino, N,N-di-lower ($C_{1-4}$) alkylamino etc.), halogen, a lower ($C_{1-4}$) alkoxy group, a lower ($C_{1-4}$) alkylthio group etc.

The aralkyl group in the above-mentioned (5) includes e.g. phenyl-lower ($C_{1-4}$) alkyl such as benzyl and phenethyl, and the aryl group in the above-mentioned (6) includes e.g. phenyl.

The aralkyl group or the aryl group described above may have e.g. halogen (e.g., F, Cl, Br etc.), nitro, an amino group which may be substituted (e.g., amino, N-lower ($C_{1-4}$) alkylamino, N,N-di-lower ($C_{1-4}$) alkylamino etc.), lower ($C_{1-4}$) alkoxy (e.g., methoxy, ethoxy etc.), lower ($C_{1-4}$) alkylthio (e.g., methylthio, ethylthio etc.) or lower ($C_{1-4}$) alkyl (e.g., methyl, ethyl etc.) at an arbitrary position on the benzene ring thereof.

Among the groups described above, the "hydrocarbon residue" in the "hydrocarbon residue which may be bound via a heteroatom and may have a substituent group" represented by $R^3$ is preferably an alkyl or alkenyl group which may be substituted (e.g., a lower ($C_{1-5}$) alkyl or lower ($C_{2-5}$) alkenyl group which may be substituted with a hydroxyl group, an amino group, halogen or a lower ($C_{1-4}$) alkoxy group), among which a lower ($C_{1-5}$) alkyl (more preferably ethyl) is preferable.

The "heteroatom" in the "hydrocarbon residue which may be bound via a heteroatom and may have a substituent group" represented by $R^3$ includes —O—, —S(O)$_m$— [m is an integer of 0 to 2], and —NR'— [R' is a hydrogen atom or lower ($C_{1-4}$) alkyl], among which —O— is preferably used.

Among those described above, $R^3$ may be bound via —O—, —S(O)$_m$—[m is an integer of 0 to 2] or —NR'— [R' is a hydrogen atom or lower ($C_{1-4}$) alkyl], and is preferably a lower ($C_{1-5}$) alkyl or lower ($C_{2-5}$) alkenyl group which may be substituted with a substituent group selected from a hydroxyl group, an amino group, halogen and a lower ($C_{1-4}$) alkoxy group, particularly preferably a lower ($C_{1-5}$) alkyl or lower ($C_{1-5}$) alkoxy, more preferably ethoxy.

Those compounds having an angiotensin II antagonistic activity represented by the formula (I) are preferably benzimidazole-7-carboxylic acid derivative or a pharmacologically acceptable salt thereof, represented by the formula (I'):

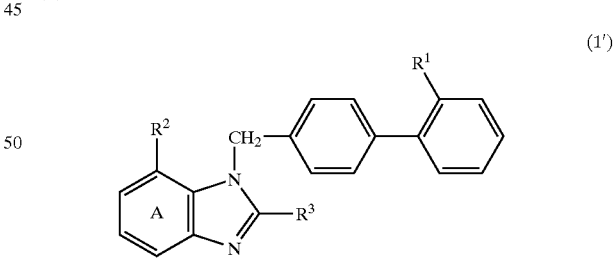

(1')

wherein $R^1$ represents (1) a carboxyl group, (2) a tetrazolyl group or (3) a group represented by the formula:

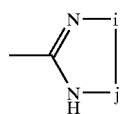

wherein i represents —O— or —S—, j represents >=O, >=S or >=S(O)$_m$ wherein m is as defined above, and ring A represents a lower ($C_{1-4}$) alkyl which may be substituted with a group besides the substituent group $R^2$ (e.g., lower ($C_{1-4}$) alkyl which may be substituted with a hydroxyl group, a carboxyl group, halogen etc.) or a benzene ring which may be substituted with halogen (preferably a benzene ring having no substituent for the substituent represented by $R^2$), and $R^2$ represents the formula —CO—D wherein D represents (1) a hydroxyl group or (2) a lower ($C_{1-4}$) alkoxy which may be substituted at its alkyl moiety by a hydroxyl group, amino, halogen, lower ($C_{2-6}$) alkanoyloxy (e.g., acetoxy, pivaloyloxy etc.), lower ($C_{3-8}$) cycloalkanoyloxy, lower ($C_{1-6}$) alkoxycarbonyloxy (e.g., methoxycarbonyloxy, ethoxycarbonyloxy etc.), lower ($C_{3-8}$,) cycloalkoxycarbonyloxy (e.g., cyclohexyloxycarbonyloxy etc.), lower ($C_{1-4}$) alkoxy or lower ($C_{3-8}$) cycloalkoxy, and $R^3$ may be bound via —O—, —S(O)$_m$— [m is an integer of 0 to 2] or —NR'— [R' is a hydrogen atom or lower ($C_{1-4}$) alkyl], and represents a lower ($C_{1-5}$) alkyl or lower ($C_{2-5}$) alkenyl group which may be substituted with a substituent selected from a hydroxyl group, an amino group, halogen and a lower ($C_{1-4}$) alkoxy group (preferably lower ($C_{1-5}$) alkyl or lower ($C_{1-5}$) alkoxy, more preferably ethoxy), and particularly preferable used are 2-ethoxy-1-[[2'-(1H-tetrazole-5-yl)biphenyl-4-yl]methyl]benzimidazol-7-carboxylic acid [Candesartan], 1-(cyclohexyloxycarbonyloxy)ethyl 2-ethoxy-1-[[2'-(1H-tetrazole-5-yl)biphenyl-4-yl]methyl]benzimidazole-7-carboxylate [Candesartan cilexetil], pivaloyloxymethyl 2-ethoxy-1-[[2'-(1H-tetrazole-5-yl)biphenyl-4-yl]methyl]benzimidazole-7-carboxylate, 2-ethoxy-1-[[2'-(2,5-dihydro-5-oxo-1,2,4-oxadiazole-3-yl) biphenyl-4-yl]methyl]benzimidazole-7-carboxylic acid or a salt thereof.

The above-described benzimidazole derivatives can be synthesized by a known method described in, for example, EP-425921, EP-459136, EP-553879, EP-578125, EP-520423, EP-668272 etc. or by an analogous method. When Candesartan cilexetil is used, stable C-type crystals described in EP-459136 are preferably used.

The compound having an angiotensin II antagonistic activity or a prodrug thereof used in the present invention may be used as it is or as a pharmacologically acceptable salt thereof. When the compound having an angiotensin II antagonistic activity has an acidic group such as a carboxyl group etc., the salt thereof includes those salts with inorganic bases (e.g., alkali metals such as sodium, potassium etc., alkaline earth metals such as calcium, magnesium etc., transition metals such as zinc, iron, copper etc.) and organic bases (e.g., organic amines such as trimethylamine, triethylamine, pyridine, picoline, ethanolamine, diethanolamine, triethanolamine, dicyclohexylamine, N,N'-dibenzyl ethylene diamine etc., basic amino acids such as arginine, lysine, ornithine etc.).

When the compound having an angiotensin II antagonistic activity has a basic group such as an amino group etc., the salt thereof includes those salts with inorganic acids and organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid etc.), acidic amino acids such as aspartic acid, glutamic acid etc., or the like.

In the present invention, a prodrug of the compound having an angiotensin II antagonistic activity [hereinafter, sometimes, referred to as AII antagonist] refers to a compound to be converted into an AII antagonist by reaction with enzymes, gastric acid etc. under physiological conditions in the living body, that is, a compound to be converted into an AII antagonist by enzymatic oxidation, reduction or hydrolysis or a compound to be converted into an AII antagonist by hydrolysis with gastric acid etc. A prodrug of an AII antagonist includes compounds derived from an AII antagonist by acylation, alkylation or phosphorylation of an amino group thereof (e.g., compounds wherein an amino group of an AII antagonist has been converted into eicosanoyl, alanyl, pentylaminocarbonyl, (5-methyl-2-oxo-1,3-dioxolene-4-yl)methoxycarbonyl, tetrahydrofuranyl, pyrrolidylmethyl, pivaloyloxymethyl, tert-butyl etc.); compounds derived from an AII antagonist by acylation, alkylation, phosphorylation or boration of a hydroxyl group thereof (e.g., compounds wherein a hydroxyl group of an AII antagonist has been converted into acetyl, palmitoyl, propanoyl, pivaloyl, succinyl, furamallyl, alanyl, dimethylaminomethylcarbonyl etc.); and compounds derived from an AII antagonist by esterifying or amidating a carboxyl group thereof (e.g., compounds wherein a carboxyl group of an AII antagonist has been converted into ethyl ester, phenyl ester, carboxymethyl ester, dimethyl aminomethyl ester, pivaloyloxy methyl ester, ethoxycarbonyloxy ethyl ester, phthalidyl ester, (5-methyl-2-oxo-1,3-dioxolene-4-yl) methyl ester, cyclohexyloxy carbonyloxy ethyl ester, methyl amide etc.). These compounds can be produced from an AII antagonist by a per se known method.

A prodrug of an AII antagonist may be the one to be converted into an AII antagonist under physiological conditions as described in "Iyakuhin no Kaihatsu" (Development of Pharmaceutical Preparations), vol. 7, "Bunshi Sekkei" (Molecular Design), pp. 163–198, published in 1990 by Hirokawa Shoten.

An AII antagonist may be a hydride or anhydride.

The compound represented by the formula (I) or a pharmaceutically acceptable salt thereof is low-toxic and can be used as an agent for preventing recurrence of cerebrovascular disorder or as an agent for ameliorating troubles following cerebrovascular disorder and inhibiting progress thereof in mammals (e.g., humans, mice, rats, rabbits, dogs, cats, cattle, pigs, monkeys etc.) as it is or as a pharmaceutical composition thereof with a pharmaceutically acceptable carrier.

The pharmaceutically acceptable carriers used in the present invention are conventional organic or inorganic carrier materials in pharmaceutical preparations, and are formulated as excipients, lubricants, binders or disintegrators in solid preparations, or as solvents, solubilizers, suspending agents, isotonizing agents, buffers and analgesics in liquid preparations. If necessary, pharmaceutical additives such as preservatives, antioxidants, coloring agents and sweeteners can also be used.

Preferable examples of the excipients include lactose, sucrose, D-mannitol, D-sorbitol, starch, α-starch, dextrin, crystalline cellulose, low-substituted hydroxypropyl cellulose, sodium carboxymethyl cellulose, gum arabic, dextrin, pullulan, light silicic anhydride, synthetic aluminum silicate, magnesium metasilicate aluminate etc.

Preferable examples of the lubricants include magnesium stearate, calcium stearate, talc and colloidal silica.

Preferable examples of the binders include pregelatinized starch, sucrose, gelatin, gum arabic, methyl cellulose, carboxymethyl cellulose, sodium carboxymethyl cellulose, crystalline cellulose, sucrose, D-mannitol, trehalose, dextrin, pullulan, hydroxypropyl cellulose, hydroxypropylmethyl cellulose, polyvinyl pyrrolidone etc.

Preferable examples of the disintegrators include lactose, white sugar, starch, carboxymethyl cellulose, calcium carboxymethyl cellulose, sodium croscarmellose, sodium carboxymethyl starch, light silicic anhydride, low-substituted hydroxypropyl cellulose etc.

Preferable examples of the solvents include injectable water, physiological saline, Ringer's solution, alcohol, propylene glycol, polyethylene glycol, sesame oil, corn oil, olive oil, cottonseed oil etc.

Preferable examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate etc.

Preferable examples of the suspending agents include surfactants such as stearyl triethanolamine, sodium laurylsulfate, lauryl aminopropionic acid, lecithin, benzalconium chloride, benzetonium chloride, and glycerine monostearate; hydrophilic polymers such as polyvinyl alcohol, polyvinyl pyrrolidone, sodium carboxymethyl cellulose, methyl cellulose, hydroxymethyl cellulose, hydroxyethyl cellulose, and hydroxypropyl cellulose; Polysorbate; and polyoxyethylene hardened sesame oil.

Examples of the isotonizing agents include sodium chloride, glycerine, D-mannitol, D-sorbitol, glucose etc.

Preferable examples of the buffers include buffers such as phosphates, acetates, carbonates and citrates.

Preferable examples of the analgesics include benzyl alcohol etc.

Preferable examples of the preservatives include paraoxybenzoates, chlorobutanol, benzyl alcohol, phenethyl alcohol, hydroacetic acid, and sorbic acid. Preferable examples of the antioxidants include sulfites, ascorbates etc.

Preferable examples of the coloring agents include water-soluble edible tar pigment (e.g., edible pigments such as Edible Red Nos. 2 and 3, Edible Yellow Nos. 4 and 5, Edible Blue Nos. 1 and 2), water-insoluble lake pigments (e.g., aluminum salts of the water-soluble edible tar pigments described above), natural pigments (e.g., β-carotene, chlorophyll, red iron oxide etc.) or the like.

Preferable examples of the sweeteners include sodium saccharine, glytylrytin [phonetic] dipotassium, aspartame, stevia etc.

The dosage form of the pharmaceutical composition includes e.g. oral preparations such as tablets, capsules (including soft capsules, microcapsules etc.), granules, powders, syrups, emulsions and suspensions; and parenteral preparations such as injectable preparations (e.g., those for subcutaneous injection, intravenous injection, intramuscular injection, intraperitoneal injection, injection into the glass body etc.), drips, preparations for external application (e.g., preparations for administration via the nose, transdermal preparations, ointments etc.), suppositories (e.g., rectal suppositories, vaginal suppositories), pellets and drips, and these can be safely administered orally or parenterally.

The pharmaceutical preparation can be produced by conventional methods in the field of pharmaceutical manufacturing, for example by methods described in the Japanese Pharmacopoeia, etc. Hereinafter, a specific process for producing the pharmaceutical preparation is described in more detail.

For example, the oral preparation can be produced by adding e.g. excipients (e.g., lactose, sucrose, starch, D-mannitol etc.), disintegrators (e.g., calcium carboxymethyl cellulose etc.), binders (e.g., pregelatinized starch, gum arabic, carboxymethyl cellulose, hydroxypropyl cellulose, polyvinyl pyrrolidone etc.) or lubricants (e.g., talc, magnesium stearate, polyethylene glycol 6000 etc.) to the active ingredient and then molding by compression, if necessary followed by coating thereof in a per se known method with a coating base with the aim of masking tastes or preparing enteric or lasting preparations.

The coating base includes e.g. a sugar coating base, a water-soluble film coating base, an enteric film coating base, a sustained release film coating base etc.

Sucrose is used as the sugar coating base, and at least one member selected from talc, precipitated calcium carbonate, gelatin, gum arabic, pullulan and carnauba wax may further be used alone or in combination.

The water-soluble film coating base includes e.g. cellulose type polymers such as hydroxypropyl cellulose, hydroxypropylmethyl cellulose, hydroxyethyl cellulose and methylhydroxyethyl cellulose; synthetic polymers such as polyvinyl acetal diethylaminoacetate, aminoalkylmethacrylate copolymer E [Eudragit E (trade name), Rhoem Pharma Ltd.], polyvinyl pyrrolidone etc.; and polysaccharides such as pullulan.

The enteric film coating base includes e.g. cellulose type polymers such as hydroxypropylmethyl cellulose phthalate, hydroxypropylmethyl cellulose acetatesuccinate, carboxymethylethyl cellulose and acetic acid phthalic acid cellulose; acrylate type polymers such as methacrylate copolymer L [Eudragit L (trade name), Rhoem Pharma Ltd.], methacrylate copolymer LD [Eudragit L-30D55 (trade name), Rhoem Pharma Ltd.] and methacrylate copolymer S [Eudragit S (trade name), Rhoem Pharma Ltd.]; and naturally occurring materials such as shellac.

The sustained release film coating base includes e.g. cellulose type polymers such as ethyl cellulose; aminoalkyl methacrylate copolymer RS [Eudragit RS-100 (trade name), Rhoem Pharma Ltd.] and acrylate type polymers such as an ethyl acrylate-methyl methacrylate copolymer suspension [Eudragit NE (trade name), Rhoem Pharma Ltd.].

Two or more of the coating bases described above may be mixed and used in a suitable ratio. For coating, e.g. sunproofing agents such as titanium oxide, iron oxide etc. may also be used.

The injectable preparation is produced by dissolving, suspending or emulsifying the active ingredient along with a dispersant (e.g., Polysorbate 80, polyoxyethylene hardened sesame oil 60 etc.), polyethylene glycol, carboxymethyl cellulose, sodium alginate etc.), a preservative (e.g., methyl parabene, propyl parabene, benzyl alcohol, chlorobutanol, phenol etc.), an isotonizing agent (e.g., sodium chloride, glycerine, D-mannitol, D-sorbitol, glucose etc.) etc. in an aqueous solvent (e.g., distilled water, physiological saline, Ringer's solution etc.) or an oil solvent (e.g., propylene glycol and vegetable oils such as olive oil, sesame oil, cottonseed oil, corn oil etc.) and the like. In this case, it is possible to use additives such as a solubilizer (e.g., sodium salicylate, sodium acetate etc.), a stabilizer (e.g., human serum albumin etc.), an analgesic (e.g., benzyl alcohol etc.) or the like.

The dose of the compound represented by the formula (I) or a pharmaceutically acceptable salt thereof is varied depending on the subject of administration, administration route, intended diseases, conditions etc., but in the case of oral administration for mammals, particularly humans (weighing 50 kg), the compound represented by the formula (I) or a pharmaceutically acceptable salt thereof as the active ingredient is usually administered in a dose of about 0.001 to 500 mg, preferably 0.1 to 50 mg, and this dose is administered preferably once to thrice every day.

The agent for preventing recurrence of cerebrovascular disorder or the agent for ameliorating troubles following cerebrovascular disorder and inhibiting progress thereof according to the present invention can be used simultaneously or at intervals with an anti-dementia agent, a nitrogen monoxide action enhancer, a glutamate inhibitor, and an inhibitor of blood vessel thickening, in addition to an agent for ameliorating cerebral circulation and blood flow, an agent for ameliorating cerebral metabolism, an agent for ameliorating mental diseases, an anti-convulsion agent, a therapeutic agent for hypertension, a therapeutic agent for diabetes, an anti-cerebral edema agent, a thrombolytic, an antiplatelet, an anticoagulant, an agent for ameliorating lipid metabolism, and a radical scavenger.

When these chemicals are used in combination, the respective chemicals can be mixed separately or simultaneously with pharmaceutically acceptable carriers, excipients, binders, diluents etc. and administered orally or parenterally as a pharmaceutical composition. When the chemicals are formed separately into preparations, the separately formed preparations can be mixed in a diluent and administered, or the separately formed preparations may be administered simultaneously or at intervals into the subject. The pharmaceutical preparation of the present invention also encompasses a kit product for mixing the separately formed preparations with a diluent just before use and administering them (e.g., an injection kit comprising ampoules containing each powdery chemical and a diluent for mixing and dissolving two or more chemicals) and a kit product for administering the separately formed preparations simultaneously or at intervals to an intended subject (e.g., a kit for administering two or more kinds of tablets simultaneously or separately at intervals, comprising chemical-containing tablets introduced into an identical or different bag provided if necessary with a column thereon for describing the time of administering the chemical).

For example, the agent for preventing recurrence of cerebrovascular disorder or the agent for ameliorating troubles following cerebrovascular disorder and inhibiting progress thereof according to the present invention can be used in combination with agents for ameliorating cerebral circulation and blood flow, such as vinpocetine and fulnaridine, agents for ameliorating cerebral metabolism, such as anilacetam and nicergoline, agents for ameliorating mental diseases, for example therapeutic agents for schizophrenia (orazapin, risperidone etc.), anti-anxiety agents (alprazolam, diazepam etc.), anti-depression agents (fluoxcetine, certraline, fluboxamine etc.), anti-convulsion agents such as diazepam, therapeutic agents for hypertension, such as derapuryl hydrochloride and manidipine hydrochloride, therapeutic agents for diabetes, such as boguribose, pyrogritazone, sulfonyl urea agents, anti-cerebral edema agents such as glycerol, thrombolytics such as tissue plasminogen activator and prourokinase, anti-platelet agents such as ticlopidine, clopidogrel, cirostazole and aspirin, anti-coagulants such as heparin, wafarin and argatroban, agents for ameliorating lipid metabolism, such as seribastatin, pravastatin and clofibrate, and radical scavengers such as vitamins E and C.

BEST MODE FOR CARRYING OUT THE INVENTION

Hereinafter, the present invention is described in more detail by reference to Examples, which however are not intended to limit the present invention.

EXAMPLES

The agent of the present invention for preventing recurrence of cerebrovascular disorder or the agent for ameliorating troubles following cerebrovascular disorder and inhibiting progress thereof which comprises as an active component the compound having an AII antagonistic activity or a salt thereof can be produced, for example, by the following formulation.

EXAMPLE 1

| Capsules | |
|---|---|
| (1) Candesartan cilexetil | 30 mg |
| (2) Lactose | 90 mg |
| (3) Crystalline cellulose | 70 mg |
| (4) Magnesium stearate | 10 mg |
| 1 capsule | 200 mg |

(1), (2), (3) and ½ of (4) are mixed, kneaded and granulated. The remainder of (4) is added thereto, and the whole is encapsulated in a gelatin capsule.

EXAMPLE 2

| Tablets | |
|---|---|
| (1) Candesartan cilexetil | 30 mg |
| (2) Lactose | 35 mg |
| (3) Corn starch | 150 mg |
| (4) Crystalline cellulose | 30 mg |
| (5) Magnesium stearate | 5 mg |
| 1 tablet | 250 mg |

(1), (2), (3), ⅔ of (4) and ½ of (5) are mixed, kneaded and granulated. The remainders of (4) and (5) are added to the granules which are then molded into a table by compression.

Experimental Example 1

Action of Candesartan cilexetil in ameliorating troubles following cerebrovascular disorder in Stroke-Prone Spontaneously Hypertensive Rat (SHRSP).
Method:
Male SHRSP are used. SHRSP are separately raised and given 1% saline solution as drinking water to promote and regulate occurrence of cerebral apoplexy. To regulate apoplexy symptoms, rats expressing the non-voluntary motility of raising the foreleg are divided one after another into a control group and a drug administration group. After the first fit, the drinking water is replaced by tap water, and then nerve symptoms are observed. During observation, the rats are examined for severity of nerve symptoms and for change in their weight. After the final administration, the rats are allowed to bleed to death under anesthesia and subjected to histological investigation.

INDUSTRIAL APPLICABILITY

The renin-angiotensin system is revealed to play an important role in the progress of cerebrovascular lesions accompanying hypertension. Then, a compound having an AII antagonistic activity (particularly Candesartan cilexetil) can be expected to inhibit cerebral arteriosclerosis and the progress of arteriosclerotic lesions (for example, carotid artery lesions) responsible for ischemic cerebrovascular disorder not only by the vasodilator action but also by the action of improving endothelial cell functions and inhibiting inner membrane thickening (correction of vascular remodeling). Further, reduction in cerebral blood flow and microcirculation in brain are ameliorated by the action of ameliorating the ability for automatic circulation of cerebral circulation, and there are further brought about various actions for protection of brain (nerves), correction of an abnormality in fibrinolytic system, amelioration of blood properties, etc. Thus, the compound is useful for preventing recurrence of cerebrovascular disorder or for ameliorating troubles following cerebrovascular disorder and inhibiting progress thereof.

That is, Candesartan cilexetil having the following actions can be used effectively as an agent for preventing recurrence of cerebrovascular disorder or as an agent for ameliorating troubles following cerebrovascular disorder and inhibiting progress thereof.

(1) Long-lasting action of reducing blood pressure without adversely influencing cerebral blood flow It is reported that Candesartan, i.e. an active metabolite of Candesartan cilexetil, can deviate the lower limit of automatic regulation leftward (toward lower blood pressure level) (Vraamark T et al., J Hypertens 13:755–761, 1995), and in a patient with cerebrovascular disorder where the ability for automatic regulation of cerebral vessels is hindered, the recurrence of cerebrovascular disorder can be prevented by preventing or decreasing cerebral ischemia by the mechanism of blood flow kinetics as a cause of the recurrence. Further, Candesartan cilexetil can prevent recurrence of cerebrovascular disorder by its stable blood pressure depressing action through 24 hours, thus stably controlling blood pressure whereby a significant reduction in blood pressure at night or an increase in blood pressure from night to early morning or in early morning, which is a cause of occurrence and recurrence of cerebrovascular disorder, is prevented. Further, Candesartan cilexetil can lower blood pressure safely to a therapeutically desired level in a patient with cerebrovascular disorder having various complications such as diabetes, cardiac diseases and renal diseases in addition to hypertension, thus significantly contributing to inhibition of the progress of organ disorders due to these complications without causing significant reduction in blood pressure, and finally the recurrence of cerebrovascular disorder can be prevented by reducing the dangerous factors for recurrence of cerebrovascular disorder.

(2) Anti-arteriosclerosis action:

It has been revealed that AII have not only a strong vasoconstricting action but also various actions such as proliferating action, inflammation action, oxidizing action, vascular penetrating action, etc., thus playing an important role in the progress of not only hypertension but also cerebrovascular lesions. That is, it is reported that AII induces hypertrophy of cells via expression of oncogenes and growth factors, thickens vascular walls by an increase in production of extracellular substrate, activates a transcriptional factor (NF-kB) to increase expression of a monocyte chemotactic factor (Hernandez-Presa M, et al., Circulation 95, 1532–1541, 1997), and induces production of free radicals from inflammatory cells (Zafari A M, et al., Hypertension 32, 488–495, 1998), thus significantly influencing various organ disorders including cerebrovascular disorder. Candesartan cilexetil not only inhibits these disorders attributable to AII thereby treating hypertension but also exerts actions for prevention of progress of arteriosclerosis, amelioration of vessel remodeling, amelioration of microcirculation, inhibition of edema, amelioration of endothelial cell functions (promotion of NO production in endothelial cells), and protection of cells thereby preventing the progress and recurrence of cerebrovascular disorder and ameliorating troubles after cerebrovascular disorder.

(3) Reduction in dangerous factors for diabetes etc.:

Candesartan cilexetil is known to improve insulin sensitivity clinically (Iimura O., et al., Am J Hypertens 8, 353–357, 1995), and can ameliorate various disorders accompanying an abnormality in glucose tolerance, diabetes and a reduction in insulin sensitivity as dangerous factors for recurrence of cerebrovascular disorder thereby preventing the progress and recurrence of cerebrovascular disorder and ameliorating troubles after cerebrovascular disorder.

(4) Brain-protecting action:

Candesartan cilexetil has actions for anti-inflammation, anti-oxidization, anti-edema, amelioration of microcirculation and improvement of endothelial cell functions as described in the above (2), and can inhibit vasoconstriction and promotion of platelet agglutination caused by various vasoconstrictor such as endothelin and thromboxane induced and enhanced by AII, whereby the penambra region can be saved by amelioration of blood flow and inhibition of cellular disorders at the acute stage of vascular infarction.

Further, it is reported that a disorder in the brain-blood barrier in an angiotensinogen knockout mouse is ameliorated by administration of an angiotensin peptide such as angiotensin IV (angiotensin 3–8) (Kakinuma Y. et al., Nat Med. 4, 1078–1080, 1998), and also that an angiotensin peptide such as AIV is related to memory and the action of increasing cerebral blood flow (Wright J W et al., Brain Res Rev 25, 96–124, 1997), and the increase in these peptides by administration of Candesartan cilexetil (decomposed products are increased by an increase in AII) can prevent the progress and recurrence of cerebrovascular disorder via the above-described actions and ameliorate troubles after cerebrovascular disorder.

(5) Influence on blood components:

It is reported that stimulation with AII causes an increase in hematocrit due to an increase in production of erythropoietin, an abnormality in the fibrinolytic system due to enhancement of the activity of plasminogen activator inhibitor type-1, and induction of expression of E-selectin in vascular endothelial cells and subsequent adherence of leukocytes (Grafe M et al., Cir Res 81, 804–811, 1997). These are inhibited by Candesartan cilexetil so that changes in blood such as coagulation of platelets, leukocytes and erythrocytes are ameliorated, while formation of thrombus is inhibited and microcirculation is ameliorated by the added or synergistic actions in improvement of endothelial cell functions (1) and inhibition of thromboxane production (4), whereby the progress and recurrence of cerebrovascular disorder can be prevented and troubles after cerebrovascular disorder can be ameliorated.

(6) Combination with other therapeutic agents:

Candesartan cilexetil can be used in combination with a thrombolytic, an antiplatelet, an anti-blood-coagulant (anticoagulant), an agent for ameliorating cerebral circulation, an agent for ameliorating cerebral metabolism and an agent for ameliorating mental diseases, and by these added or synergistic actions, further excellent effects can be expected, and the dose of these agents and the frequency of administration thereof can be decreased thereby reducing side effects attributable to these chemicals.

What is claimed is:

1. A method for preventing recurrence of cerebrovascular disorder in a mammal, which comprises administering an effective amount of a compound having an angiotensin II antagonistic activity, a prodrug thereof or a salt thereof to the mammal, wherein the compound having an angiotensin II antagonistic activity is a compound represented by the formula (I):

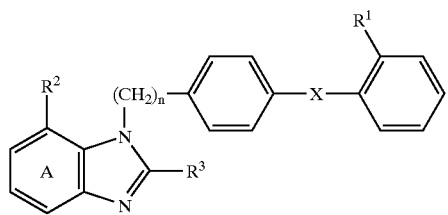

wherein R¹ represents a group capable of forming an anion or being converted into said group, X indicates that the phenylene group and the phenyl group are bound to each other directly or via a spacer of a chain made of 2 or less atoms, n is an integer of 1 or 2, ring A represents a benzene ring which may further have substituent(s), R² represents a group capable of forming an anion or being converted into said group, and R³ represents a hydrocarbon residue which may be bound via a heteroatom and may have substituent(s).

2. The method according to claim 1, wherein the compound having an angiotensin II antagonistic activity is Candesartan cilexetil, or Candesartan.

3. The method according to claim 1, wherein the compound having an angiotensin II antagonistic activity is 2-ethoxy-1-[[2'-(1H-tetrazole-5-yl)biphenyl-4-yl]methyl]benzimidazole-7-carboxylic acid.

4. The method according to claim 1, wherein the compound having an angiotensin II antagonistic activity is 1-(cyclohexyloxycarbonyloxy)ethyl 2-ethoxy-1-[[2'-(1H-tetrazole-5-yl)biphenyl-4-yl]methyl]benzimidazole-7-carboxylate.

5. The method according to claim 1, wherein the compound having an angiotensin II antagonistic activity is 2-ethoxy-1-[[2'-(2,5-dihydro-5-oxo-1,2,4-oxadiazole-3-yl)biphenyl-4-yl]methyl]benzimidazole-7-carboxylic acid.

* * * * *